United States Patent
Pinsker

[11] Patent Number: 5,990,175
[45] Date of Patent: *Nov. 23, 1999

[54] PREVENTION OF MIGRAINE

[76] Inventor: Walter Pinsker, 21 Skookwams Ct., West Islip, N.Y. 11795

[*] Notice: This patent is subject to a terminal disclaimer.

[21] Appl. No.: 09/042,931

[22] Filed: Mar. 17, 1998

Related U.S. Application Data

[63] Continuation of application No. 08/693,158, Oct. 4, 1996, Pat. No. 5,753,712.

[51] Int. Cl.⁶ .......................... A61K 31/52; A61K 31/135
[52] U.S. Cl. .............................................. 514/649; 514/816
[58] Field of Search ...................................... 514/649, 816

[56] References Cited

U.S. PATENT DOCUMENTS 3,819,706  6/1974  Mehta ................................. 260/570.5
3,885,046  5/1975  Mehta ..................................... 424/330

*Primary Examiner*—Shep K. Rose
*Attorney, Agent, or Firm*—Dike, Bronstein, Roberts & Cushman, LLP; George W. Neuner

[57] ABSTRACT

A method of preventing migraine headaches in humans by the administration of the compound of the formula I

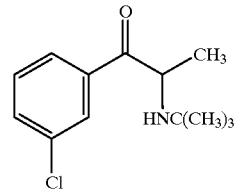

(I)

or a pharmaceutically acceptable acid addition salt thereof in a non-toxic, effective therapeutic amount (calculated as base) to a human in need thereof.

2 Claims, No Drawings

PREVENTION OF MIGRAINE

This apllication is a continuation of Ser. No. 08/693,158 filed Oct. 4, 1996, now U.S. Pat. No. 5,753,712.

BACKGROUND OF THE INVENTION

This invention is directed to a method of treatment of migraine headaches in humans by the administration to the humans of the compound of the formula I

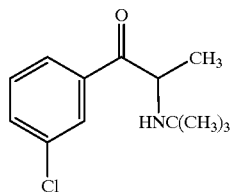

(I)

or a pharmaceutically acceptable acid addition salt thereof in a non-toxic, therapeutic amount (calculated as base) to a human in need thereof.

In U.S. Pat. No. 3,819,706 and 3,885,046 m-chloro-α-t-butylaminopropiophenone and salts thereof, in particular the hydrochloride salt, were disclosed on being antidepressants. Bupropion hydrochloride is the generic name for m-chloro-α-t-butylarninopropiophenone which is used under the trademark WELLBUTRIN® in the United States of America for the treatment of depressions. The neurochemical mechanism of the antidepressant effect of bupropion is not known.

I have now found that bupropion hydrochloride is effective in treating migraine headaches in humans. It is effective when administered alone or together with caffeine, e.g., with one or two cups of coffee.

The compound of formula (I) (the active ingredient) or the pharmaceutically acceptable acid addition salt thereof is preferably administered in unit dosage form to the human being treated.

A pharmaceutical composition containing a compound of formula (I), or a pharmaceutically acceptable salt thereof, may be presented in discrete units such as tablets, capsules, ampules or suppositories, each containing an effective-amount of the compound or salt for treatment of migraine.

As an example, for the treatment of humans having migraines the preferred unit dosage of a compound of formula (I) as the hydrochloride salt thereof for oral administration is about 10 mg to 450 mg, preferably 50 mg to 300 mg, and the most preferred unit dosage of 100 to 200 mg optionally given in divided doses. Treatment is preferably initiated at the first (prod romal) symptom of a migraine.

The compound of formula (I) may also be administered prophylactically, e.g., at a preferred dose of 100 mg per day, especially for patients suffering frequent migraines.

A compound of formula (I) or pharmaceutically acceptable salts thereof may be presented as an oral unit preparation (for example as a cachet, tablet or capsule) containing one or more pharmaceutically acceptable carriers which may take the form of solid diluents such as lactose, cornstarch, micronized silica gel as well as other excipients known in the art.

It should be understood that in addition to the aforementioned ingredients, the pharmaceutical composition of this invention may include one or more of additional ingredients e.g., pharmaceutically acceptable carriers such as diluents, buffers, flavouring agents, binders, surface active agents, thickeners, lubricants, preservatives, and the like. The formulations may be prepared by admixture of the ingredients, and, if necessary, shaping the resulting mass, and filling into suitable containers.

A preferred pharmaceutical formulation comprises bupropion hydrochloride (100 mg) and caffeine (200 mg) and a pharmaceutically acceptable carrier therefor.

The compound used in this invention is preferably presented for use as a pharmaceutically acceptable acid addition salt. Examples of some of the pharmaceutically acceptable salts which can be utilized are salts of the following acids: hydrochloric, sulfuric, phosphoric and toluenesulphonic.

Reference should be had to U.S. Pat. No. 3,819,706 and 3,885,046, which are incorporated herein by reference hereto for a description of the preparation of the compound of formula (I), acid addition salts thereof, tablets, capsules, parenteral solutions and suppositories incorporating same.

I claim:

1. A method of preventing migraine in a human suffering from migraine, but not depression, which comprises administering an effective migraine preventing amount of bupropion hydrochloride.

2. The method of claim 1, wherein the effective migraine preventing amount of bupropion hydrochloride is 100 mg per day.

* * * * *